US006613018B2

(12) United States Patent
Bagga et al.

(10) Patent No.: US 6,613,018 B2
(45) Date of Patent: Sep. 2, 2003

(54) SYSTEM AND KIT FOR DELIVERY OF RESTORATIVE MATERIALS

(75) Inventors: Charanpreet S. Bagga, Phoenixville, PA (US); Antony Koblish, Malvern, PA (US); Maarten Persenaire, Phoenixville, PA (US); Erik M. Erbe, Berwyn, PA (US)

(73) Assignee: Vita Licensing, Inc., Wilmington, DE (US)

( * ) Notice: Subject to any disclaimer, the term of this patent is extended or adjusted under 35 U.S.C. 154(b) by 0 days.

(21) Appl. No.: 09/788,943

(22) Filed: Feb. 20, 2001

(65) Prior Publication Data

US 2002/0120240 A1 Aug. 29, 2002

(51) Int. Cl.[7] .............................................. A61M 5/00
(52) U.S. Cl. ....................................................... 604/187
(58) Field of Search ............................. 604/264, 93.01, 604/117, 164.01–164.04, 173, 523, 272, 187, 181

(56) References Cited

U.S. PATENT DOCUMENTS

| | | | | |
|---|---|---|---|---|
| 4,230,123 A | * | 10/1980 | Hawkins, Jr. | 128/658 |
| 4,469,109 A | | 9/1984 | Mehl | 128/753 |
| 4,737,146 A | * | 4/1988 | Amaki et al. | 604/51 |
| 4,793,363 A | | 12/1988 | Ausherman et al. | 128/754 |
| 4,838,282 A | | 6/1989 | Strasser et al. | 128/754 |
| 5,195,974 A | * | 3/1993 | Hardy | 604/110 |
| 5,595,172 A | * | 1/1997 | Reese | 128/200 |
| 5,601,559 A | | 2/1997 | Melker et al. | 606/79 |
| 5,685,852 A | * | 11/1997 | Turkel et al. | 604/159 |
| 5,702,373 A | * | 12/1997 | Samson | 604/282 |
| 5,795,332 A | * | 8/1998 | Lucas et al. | 604/96 |
| 6,019,765 A | | 2/2000 | Thornhill et al. | 606/94 |
| 6,019,776 A | | 2/2000 | Preissman et al. | 606/185 |
| 6,033,411 A | | 3/2000 | Preissman | 606/99 |
| 6,048,343 A | | 4/2000 | Mathis et al. | 606/72 |
| 6,231,615 B1 | | 5/2001 | Preissman | 623/23.73 |
| 6,241,734 B1 | | 6/2001 | Scribner et al. | 606/93 |
| 6,248,110 B1 | | 6/2001 | Reiley et al. | 606/93 |
| 6,273,916 B1 | | 8/2001 | Murphy | 623/23.62 |

OTHER PUBLICATIONS

Chiras, J., et al., "Percutaneous Vertebroplasty," *J. Neuroradiol.*, 1997, 24, 45–59 (English translation).
Deramond, H., et al., "Percutaneous Vertebroplasty," *Seminars in Musculoskeletal Radiology*, 1997, 1(2), 285–295.
Gangi, A., et al., "Percutaneous vertebroplasty guided by a combination of CT and fluoroscopy," *AJNR*, Jan. 1994, 83–86.
Heini, P.F., et al., "Percutaneous transpedicular vertebroplasty with PMMA: operative technique and early results," *Eur. Spine J.*, 2000, 9, 445–450.
Jensen, M.E., et al., "Percutaneous polymethylmethacrylate vertbroplasty in the treatment of osteoporotic vertebral body compression fractures: technical aspects," *AJNR*, Nov. 1997, 18, 1897–1904.

* cited by examiner

*Primary Examiner*—Brian L. Casler
*Assistant Examiner*—Ann Y Lam
(74) *Attorney, Agent, or Firm*—Woodcock Washburn LLP

(57) ABSTRACT

Novel kits are provided for the delivery of restorative compositions into an intraosseous space or surgical defect comprising cannulae for accessing an intraosseous space, mandarins insertable into the cannulae and movable therein, catheters and a system for the delivery of aliquots of restorative compositions into the space via the catheters.

14 Claims, 6 Drawing Sheets

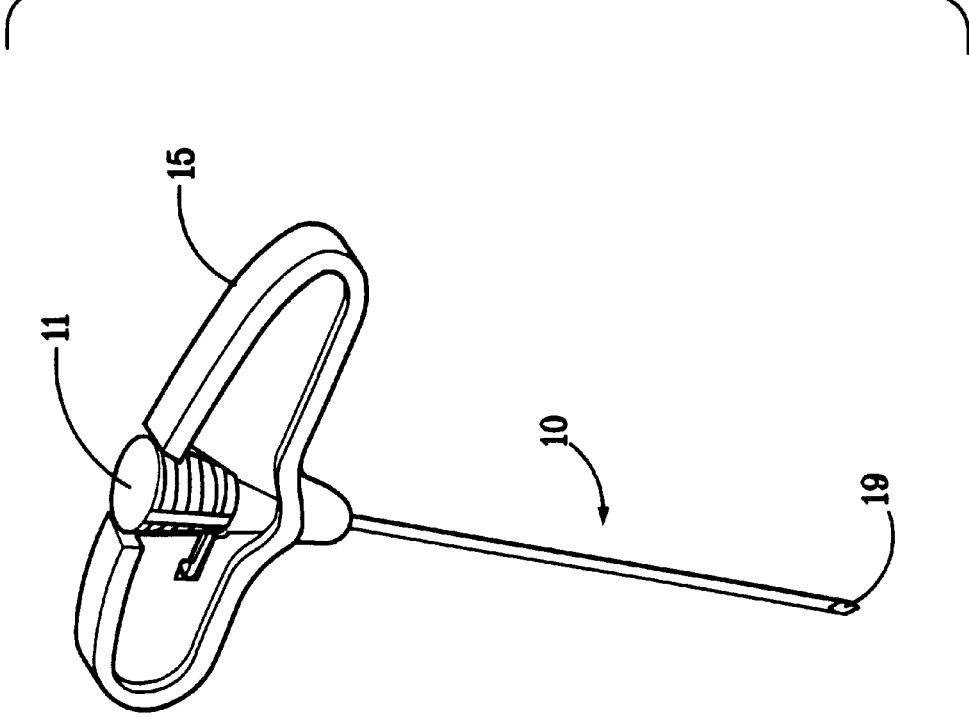
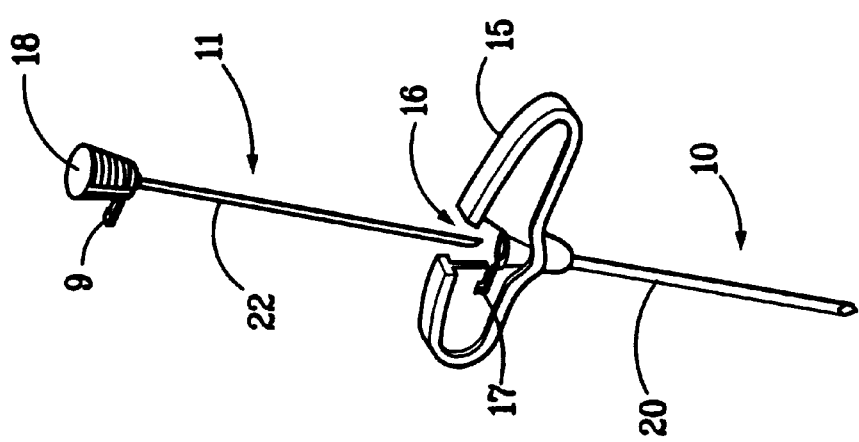
FIG. 2

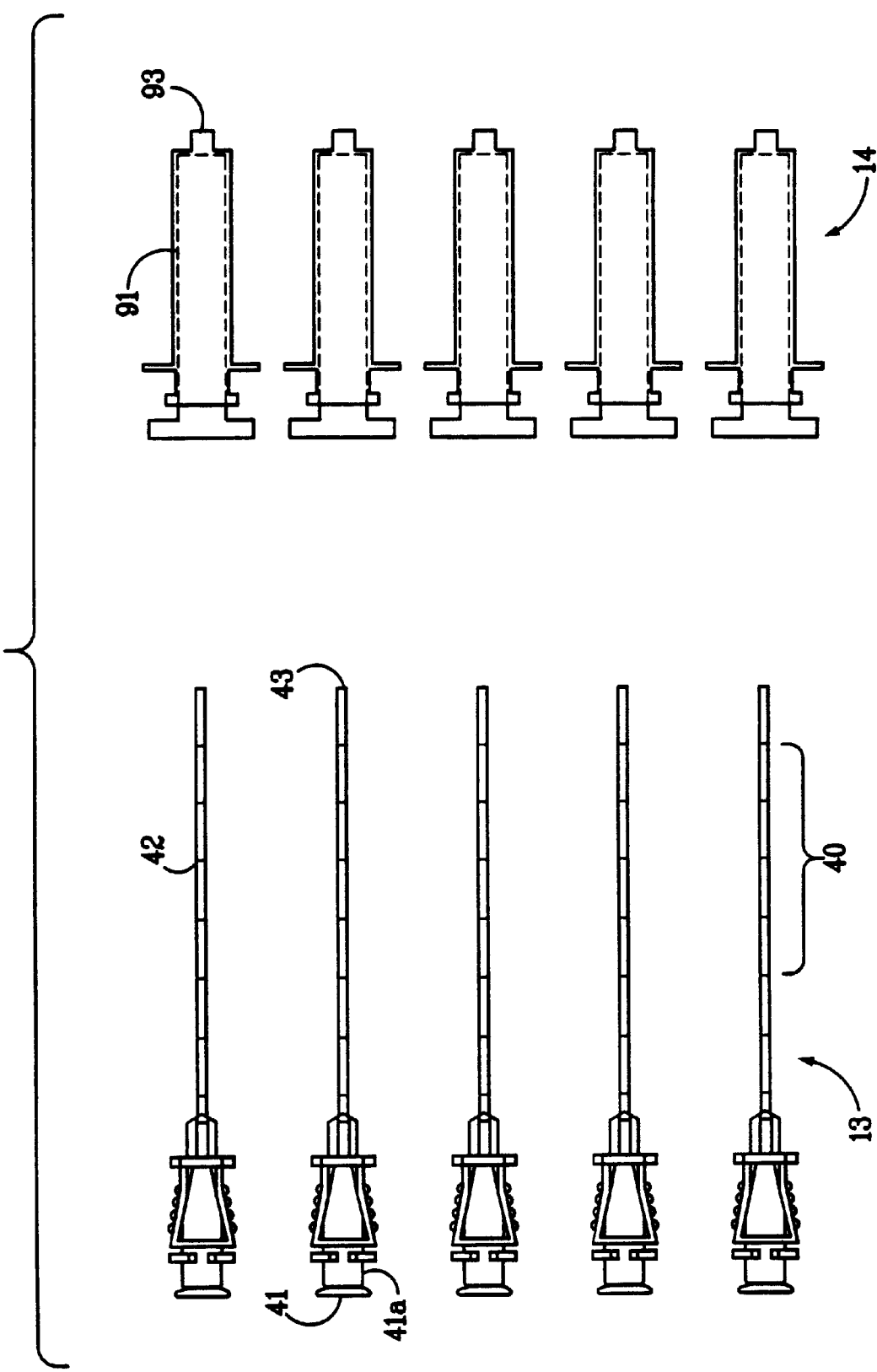

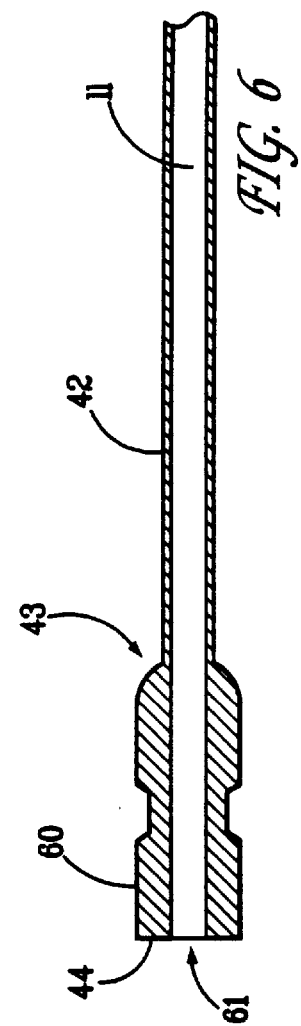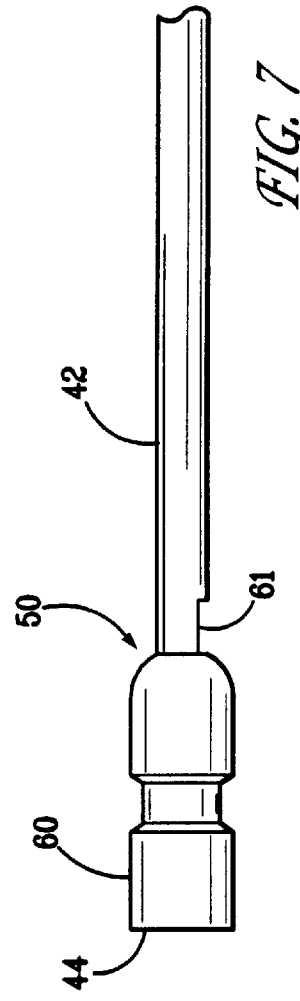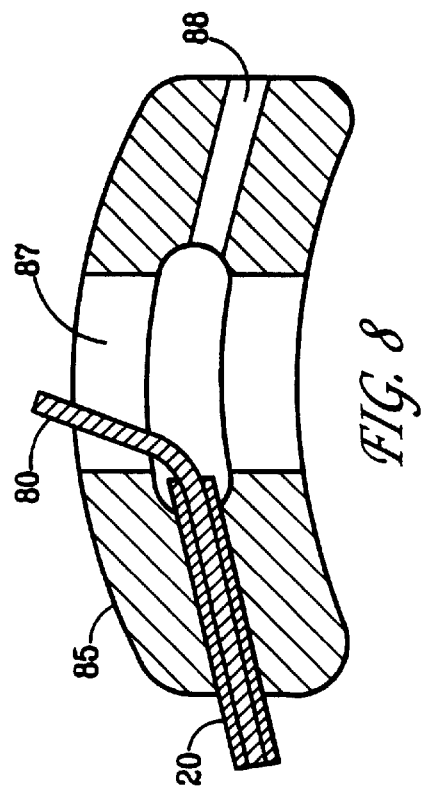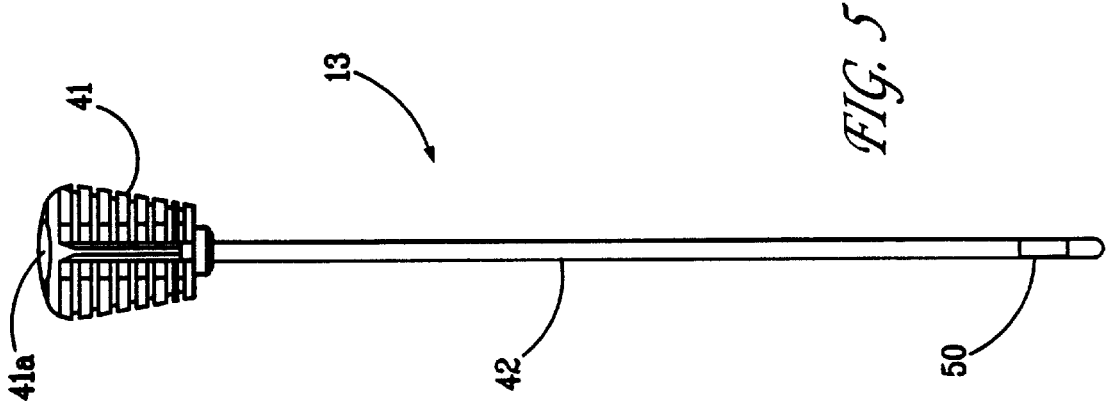

SYSTEM AND KIT FOR DELIVERY OF RESTORATIVE MATERIALS

FIELD OF THE INVENTION

This invention relates to kits for the delivery of restorative compositions into an intraosseous space, especially kits, usable in percutaneous surgical procedures, such as percutaneous vertebroplasty. This invention is also directed to systems for the delivery of aliquots of restorative compositions into a desired space especially via catheters. The kits may further comprise needles/cannulae, stylets/mandarins and/or syringes.

BACKGROUND OF THE INVENTION

Percutaneous surgical procedures have come to the forefront of the orthopaedic and neurological surgery fields, in an effort to limit exposure of tissues, reduce operating time, speed up recovery time and minimize patient scarring. Percutaneous vertebroplasty is a procedure by which, currently, acrylic cement, typically polymethylmethacrylate ("PMMA"), is injected into the vertebral body by a percutaneous route in order to prevent vertebral body collapse and pain in patients with unhealthy vertebral bodies. Percutaneous injection has been indicated as a means of pain relief and restoration in patients with vertebral hemangiomas, painful vertebral body tumors, as well as painful osteoporosis with loss of height and/or compression fractures of the vertebral body. See, e.g., Gangi, A., et al. *Percutaneous Vertebroplasty Guided by a Combination of CT and Fluoroscopy*, AJNR 15:83–86, January 1994 ("Gangi"). All references cited in this specification are incorporated herein by reference. Percutaneous injection is also minimally invasive compared to the alternative of exposing the entire soft and hard tissue at the surgical site.

U.S. Pat. Nos. 6,033,411 and 6,019,776 to Preissman, et al. disclose methods for controlled approach to the interior of a vertebral body by inserting a threaded or sharp-pointed mandarin and cannula percutaneously through the soft tissue of an organism until abutting the soft tissue; further inserting the mandarin into a predetermined location within the hard tissue; ratcheting a pawl mechanism or rotating a camming mechanism to advance the cannula along the mandarin to the predetermined location; withdrawing the mandarin from the cannula and attaching a source of implantable material for injection of the material into the organism through the cannula.

U.S. Pat. No. 4,838,282 to Strasser, et al. ("Strasser") discloses a bone biopsy needle assembly for withdrawing samples of bone, bone marrow and other such fluids, which includes a cannula and stylet. The handles of the cannula and stylet are provided with features for mating reception when assembled together. In addition, both the cannula and stylet handles are comprised of two equal generally rectangular halves extending in diametrically opposed directions from the cannula axis.

U.S. Pat. No. 4,793,363 to Ausherman, et al. ("Ausherman") discloses a bone marrow biopsy device that includes a cannula member and a stylet member with a Luer-lock connector and handle locking arrangement.

U.S. Pat. No. 4,469,109 to Mehl ("Mehl") discloses a bone marrow aspiration needle including a cannula, with a cannula housing which supports the cannula, and a partially threaded lower member, and a stylet, with a stylet cap which supports the stylet and a threaded depth stop for engaging over the cannula.

U.S. Pat. No. 5,601,559 to Melker, et al. ("Melker") discloses an intraosseous needle having a threaded shaft with two side ports, which allow fluids to pass through the needle, and a tip having a plurality of cutting edges.

Heini, P. F. et al., *Percutaneous Transpedicular Vertebroplasty with PMMA: Operative Technique and Early Results: A Prospective Study for the Treatment of Osteoporotic Compression Fractures*, Eur.Spine J. (2000) 9:445–450 ("Heini"), discusses the use of various components for performing percutaneous transpedicular vertebroplasty including a 2.0 mm K-wire for accessing the center of the vertebral body and a bone marrow biopsy needle placed over the K-wire (which is subsequently removed) for positioning the needle. Heini also discloses the use of 2-cc standard syringes for injecting the material through the needle.

Gangi describes the percutaneous injection of PMMA into the vertebral body with the aid of CT and/or fluoroscopic guidance using a needle and 2-ml Luer-lock syringe mounted on a pressure regulator to facilitate the injection of the material.

Chiras, J., et al., *Percutaneous Vertebroplasty*, J Neuroradiol, 1997, 24, 45–59 ("Chiras") discloses cannulae of 10 to 15 cm in length with a beveled edge lumen and diameter of 3 mm as being standard equipment for vertebroplasty.

Deramond, H., et al., *Percutaneous Vertebroplasty*, Seminars In Musculoskeletal Radiology, Vol. 1, No. 2, 1997: 285–295 ("Deramond"), discloses the use of various materials for percutaneous vertebroplasty ("PVP") including ten-gauge needles, 10 to 15 cm long, with a beveled extremity, fifteen-gauge needles, 5 to 7 cm long, with a tapered tip, Luer-lock syringes of 2 or 3 cc, a syringe handle and bone cement. Deramond suggests that leakage can be avoided by making injections under lateral fluoroscopic control or inserting the cannula into the lateral part of the vertebral body.

Jensen, M. E., et al., *Percutaneous Polymethylmethacrylate Vertebroplasty in the Treatment of Osteoporotic Vertebral Body Compression Fractures: Technical Aspects*, AJNR 18:1897–1904, November 1997 ("Jensen") discusses the use of various components for performing vertebroplasty procedures including a disposable 11-gauge Jamshidi needle and stylet for accessing a desired space, and both 10-ml and 1-ml syringes and an 18-gauge needle for the injection of material through the needle. Jensen, et al. teaches that the material should be allowed to set only if a leak should occur.

In the art, if a leak is detected, the operator either stops the procedure altogether, continues with the injection of more material using a different "batch" of material, or allows the material that already has been injected to thicken Clinically, using a different "batch" of material requires the surgeon to open another "batch" of material, which is costly and not desirable or practical in the case of standard restorative materials such as PMMA. Often in the case of a leak, the surgeon does not allow the material to set, but rather waits until the material reaches a pasty stage (thicken) prior to injecting more material. This approach, however, prevents the surgeon from injecting the desired amount of material, since once the material becomes pasty, he has little time to work and must forcefully inject additional material prior to the material setting in the cannula. If the material hardens in the cannula, the cannula will have to be removed and reinserted for additional doses. Surgeons are very skeptical about doing this because of the extreme difficulty in reinserting another cannula in the same exact place as the one removed.

Accordingly, it is the principle object of this invention to provide kits for minimally invasive delivery of restorative composition into an intraosseous space.

Additional objects, advantages and novel features of this invention will become apparent to those skilled in the art upon examination of the following descriptions, figures and claims thereof, which are not intended to be limiting.

SUMMARY OF THE INVENTION

This invention relates to device combinations and packaged kits for the delivery of a restorative composition into an intraosseous space. These comprise one or more cannulae adapted for accessing said intraosseous space; one or more stylets/mandarins insertable into the hollow cavity of the cannula and being movable therein to advance the cannula into position. These are adapted for accessing said intraosseous space. The kits and systems preferably also have one or more catheters that are insertable into the cannulae; and a system for delivery of aliquots of said restorative composition into the intraosseous space via the catheters. The kits can also include a micro-reamer that fits within the hollow cavity of the cannula (after removal of the stylet and before insertion of the catheter) to make a channel for material delivery via the catheter. Fixed to the proximate end of each of the cannulae, stylet, and micro-reamer is a substantially lateral surface (flat, solid knob or pedestal) responsive to impact blows. The cannula, micro-reamer and catheter may also include gradations.

The catheters of the present invention have a distal end and at least one placement orifice disposed proximate to the distal end, wherein the placement orifice may be adapted for dispensing the restorative composition directly from the distal end or radially therefrom. Catheters used in the kits may comprise stainless steel, polyimide, latex, silicone, vinyl, or polymers other than those listed herein. They may be flexible for maneuverability and be long and of such material that they can be cut to size at the time of use.

The kits can preferably further comprise a plurality of syringes having an aperture on a distal end providing fluidic passage therethrough from a bore being engageable within said aperture; as well as a locking mechanism, such as a Luer-lock type of locking mechanism, for engaging a proximal end of the catheter for dispensing of the material into the space through the catheter. In a preferred embodiment, the kit includes a plurality of syringes including a 1 cc, 3 cc and 5 cc syringes.

This invention also relates to a system for the delivery of a restorative composition to specific intraosseous space wherein the placement of aliquots of said restorative composition is under tactile feedback control of a human operator, such as a surgeon or interventionalist. The restorative composition can comprise a hydrogel, synthetic bone void filler, polymethylmethacrylate, or replicated bone marrow.

BRIEF DESCRIPTION OF THE DRAWINGS

FIG. 2 depicts a cannula/stylet locking mechanism.

FIG. 4 depicts a kit of the present invention showing a plurality of catheters and syringes.

FIG. 5 depicts the side-opening feature of certain preferred catheters of the present invention.

FIG. 6 depicts a front-opening catheter/cannula having a micro-reamer feature.

FIG. 7 depicts a side-opening catheter having a micro-reamer feature.

FIG. 8 depicts a shape memory embodiment of the catheter/micro-reamer.

Figure 1:
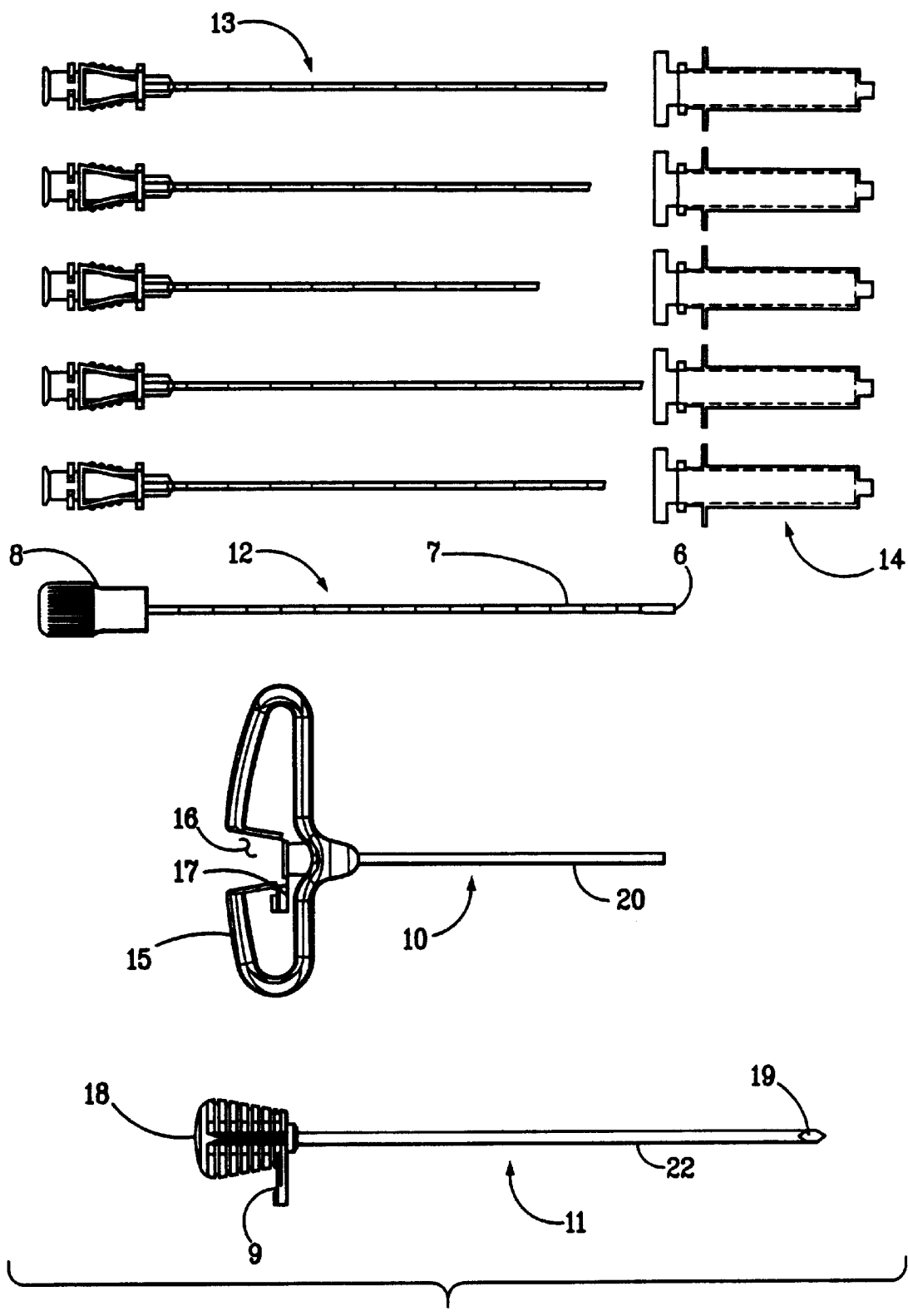
FIG. 1 depicts a kit of an embodiment of the present invention showing a cannula and stylet, a micro-reamer, and a plurality of catheters and syringes.

The present invention provides kits for the delivery of a restorative composition. Typically, the kits, such as the kit shown, for example, in FIG. 1, comprise at least a cannula 10 or needle. More typically, the cannula is adapted for accessing particular intraosseous spaces. In accordance with one embodiment, the cannula 10 is an 8 to 14 gauge, or preferably an 11 to 12-gauge needle having a solid handle 15 for absorbing impact and force upon insertion into bone, and a hollow bore 20 component attached thereto. The handle 15 preferably is asymmetrically shaped to accommodate a user's hand and includes a space 16 for receiving an unidirectional stylet/mandarin 11 (or other instruments).

Figure 3:
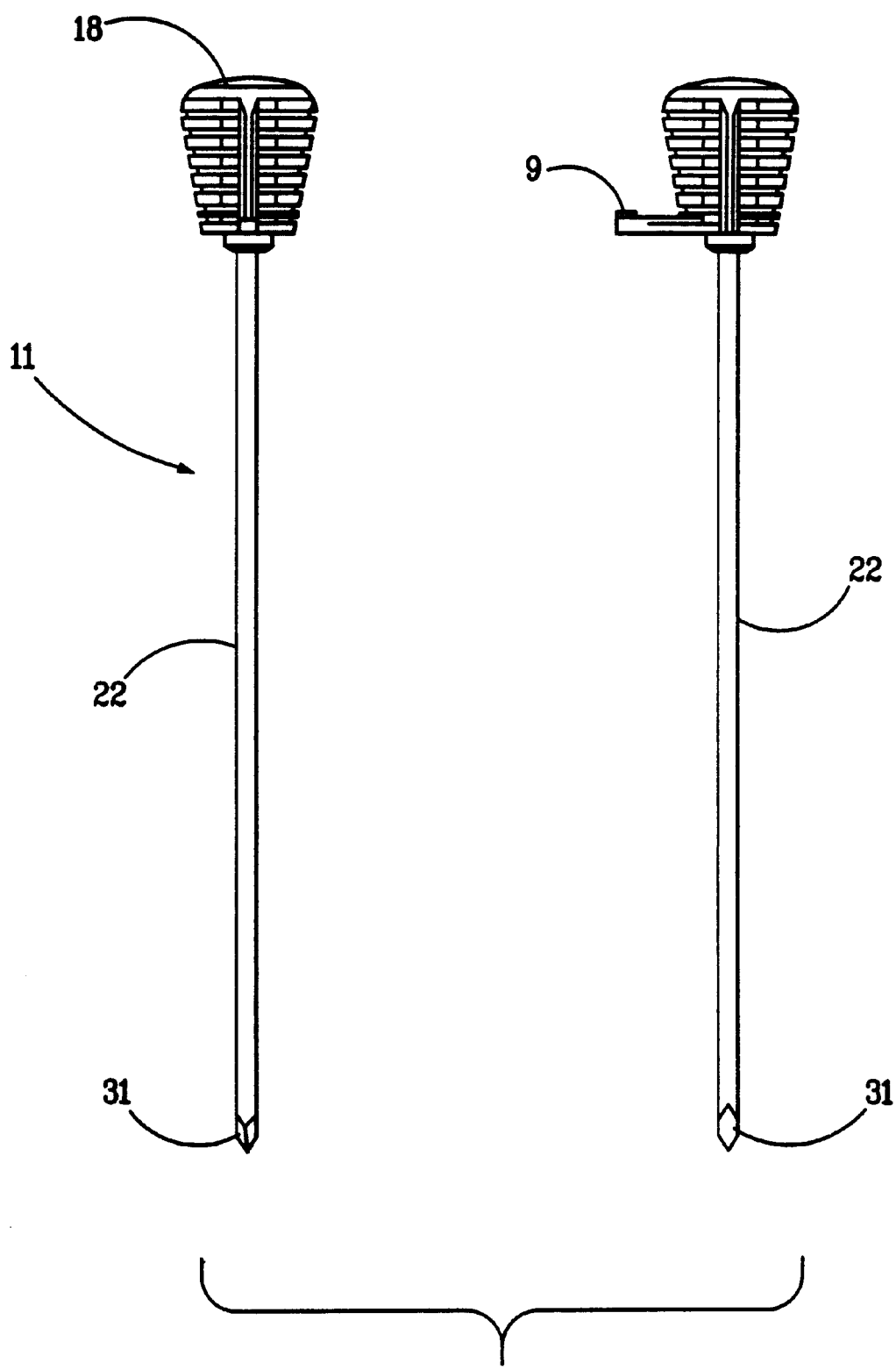
FIG. 3 depicts an alternative embodiment stylet tip.

One or more stylets 11 adapted for accessing an intraosseous space are preferred in some embodiments. Typically, the stylet 11 comprises a solid, impactable knob or head 18, which is tapered for easy insertion and removal into the receiving space 16 of the handle 15 of the cannula 10, and an elongated solid stem 22 with a beveled tip 19 (for steering capabilities) or diamond tip 31 that sits within the bore 20 of the cannula 10 when in use (see, for example, FIG. 3). The unidirectional fit allows for a pin 9 within the knob 18 of the stylet 11 to lock within a corresponding recess 17 on the handle 15 of the cannula 10 (see, for example, FIG. 2). Specifically, mating occurs when the pin 9 of the stylet 11 is simultaneously displaced in the superior/inferior direction and rotated into the recess 17 of the cannula handle 15. This fit ensures that the stylet is always positioned correctly, thus creating a solid sharp beveled tip 19 or diamond tip 31. The cannula 10 and stylet 11 are used to gain access into the body cavity. Force from either screwing or tapping is used to propel both the cannula 10 and stylet 11 into the osseous space.

Once the space is accessed by the cannula 10 and stylet 11, in some preferred embodiments, the stylet 11 is removed and a micro-reamer 12 is inserted to create room or an opening in the bone for placement of the restorative composition. The micro-reamer 12 conveniently has a knob 8 similar to that of the stylet knob 18 but without a pin being engageable within the cap of the needle. The absence of the pin allows the operator to insert and rotate the micro-reamer 12 about the space. In many forms of this invention, the micro-reamer 12 is used to create a channel, which facilitates the insertion of the catheter (and subsequently, material delivery). The rotation of the micro-reamer 12 creates some debris that helps block the venous pathways, and thus reduce the potential for leakage. In other forms of this invention, the micro-reamer 12 is fitted with a cutting means 6.

Once the space is accessed by the cannula 10 and stylet 11, in some preferred embodiments, the stylet 11 is removed and a micro-reamer 12 is inserted to create room or an opening in the bone for placement of the restorative composition. The micro-reamer 12 conveniently has a knob 8 similar to that of the stylet knob 18 but without a pin being engageable within the cap of the needle. The absence of the pin allows the operator to insert and rotate the micro-reamer 12 about the space. In many forms of this invention, the micro-reamer 12 is used to create a channel, which facilitates the insertion of the catheter (and subsequently, material delivery). The rotation of the micro-reamer 12 creates some debris that helps block the venous pathways, and thus reduce the potential for leakage. In other forms of this invention, the micro-reamer 12 is fitted with a cutting means 6. The invention may also include a cannulated screw that has a bore along the longitudinal axis for accessing the osseous space. Restorative material may be injected through this bore.

Once the micro-reamer 12 creates a space for the material, it is removed from the cannula 10 and replaced with a catheter 13. Catheters are used to deliver the restorative composition into the intraosseous space. In one specific embodiment of this invention, a front-opening catheter 43 (see FIG. 4) is provided for delivery, and in another embodiment, a side-opening catheter 50 (see FIG. 5) is provided for radial delivery of the composition within an osseous space. The front-opening allows direct injection of the material into the site through the opening in the distal tip. The side-opening catheter 50 is useful for radial delivery of the composition within an osseous space since it allows for 360° directional control of the delivery of the restorative materials. In typical embodiments, the catheters also include gradations or gradients 40 along the shaft to further aid in the delivery of the composition. These gradients 40 aid in the determination of the volume of restorative composition being injected and also the depth of the catheter within the space. Typically, the gradients 40 are placed at varying lengths suitable for each procedure and can be internal markings or external protrusions. More typically, these gradients 40 are made 1 cm apart and are external markings. The catheters of the present invention can be of varying volumes and lengths. It is appreciated the distance the micro-reamer 12 extends out of the distal tip of the cannula 10 will vary depending on the nature of the space being accessed.

Generally, the catheters are comprised of metals, such as stainless steel or titanium, which are rigid and readily visible by X-Ray; but may also be comprised of a plastic or polyimide, which can serve as a flexible element; latex; silicone; vinyl; or polymers other than those listed herein; or of a ceramic material. In other embodiments of the invention, the catheters are comprised of nitinol, or any other "shape memory" alloy. In this manner, the shape memory catheter 80 (or shape memory micro-reamer) could be placed through the cannula 20 into a structure, either an implant structure 85 or anatomical structure, with known openings 87, 88, which the shape memory catheter traverses for precise, directional delivery of material (see, for example, FIG. 8). In still more embodiments, the catheter is flexible for maneuverability and of such material that it can be cut to size at the time of use.

In accordance with a specific embodiment of this invention, the catheter 13 has a knob 41 which has an adapter 41a for connecting to a syringe tip, such as a Luer-lock and a hollow shaft 42 extending therefrom (see FIG. 4). In some preferable embodiments, the catheter can be long (to distance the surgeon or user from any source of radiation that may be used during the surgical process). In other embodiments the catheter has two consecutive shafts with one having a plunger mechanism and the second shaft being engageable to the distal end of the first shaft by means of a Luer lock or other locking means better equipped to ensure non-leakage of the restorative composition.

In one specific embodiment such as the embodiment depicted in FIG. 6, the catheter is provided with protrusions or cutting elements on its distal end 44. In this manner, the catheter acts both as a micro-reamer and catheter. This feature can be added to both the front-opening catheter 43 (see FIG. 6) and side-opening catheter 50 (see FIG. 7) embodiments. More specifically, when added to the side-opening catheter 50, the cutting means 60 is attached to the distal end 44 so that the opening 61 (upon removal of the stylet 11) is more proximal to the handle than the cutting means 60. When added to the front-opening catheter 43, the cutting means 60 is more proximal to the handle than the opening 61. While in use, the stylet 11 is kept in place during the micro-reaming aspect of the procedure, and then removed for the injection of the material. The cannula of the present invention could also be provided with means for cutting in the same manner as the front opening catheter.

By providing kits with a catheter, the present invention overcomes the situation in which a procedure is halted due to leakage, the material hardens in the cannula and the cannula must be removed and replaced, or the situation in which the material thickens and becomes difficult to inject. In many embodiments, the kits of the present invention are provided with a plurality of catheters, which fit through the cannula. Once the material hardens, the first catheter is simply removed with the cannula in place and a new catheter is slipped in place for the next dose. Typically, the cannula never has to be removed and the operator does not run the risk of trying to reinsert the cannula in the same exact place.

Figure 9:
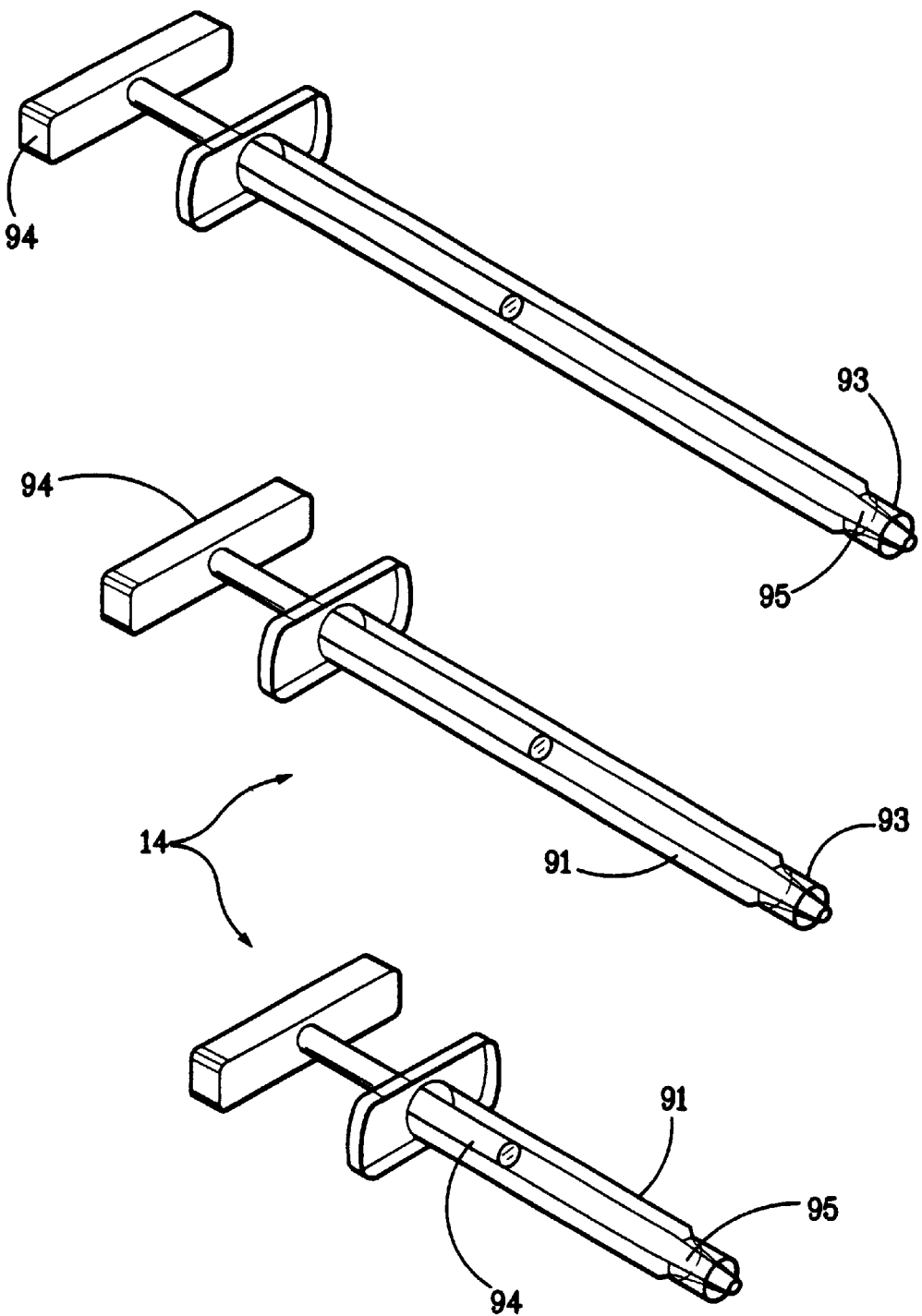
FIG. 9 depicts certain preferred syringes of the present invention kit.

In one embodiment such as the embodiment shown in FIG. 9, a syringe 14 attaches to the catheter for delivery of the material. Typically, a number of syringes are provided with the kits of the present invention, including standard, for example, 1 cc, 3 cc and 5 cc syringes. More typically, the syringes have an aperture 93 on one end for providing fluidic passage therethrough from a bore 95 being engageable within said aperture 93, and a plunger 94 that sits within the barrel 91 of the syringe 14. Material to be injected (not shown) is placed in the barrel 91 of the syringe 14 and then the plunger 94 is placed within the barrel 91 for material extrusion. The aperture 93 can be a Luer-lock type mechanism for engaging the proximal end of a catheter for injecting the restorative material into the space. In a preferred embodiment of the present invention, the 1 cc, 3 cc and 5 cc syringes are specially designed such that the diameters of the respective plungers 94 and the internal diameters of the respective barrels 91 are reduced, but are both the same size for each of the syringe sizes—1 cc, 3 cc and 5 cc syringes. Since the internal diameters of the barrels 91 of each of the different size syringes is the same, the volume differences between the syringes are compensated for by increasing the length of the syringe 14 barrel with increasing syringe size.

The amount of force required to inject material through the present invention syringes is generally reduced in each individual syringe since the cross-sectional area is reduced and the barrel 91 internal diameter and bore 95 diameter are closely matched. To further reduce the force required to move the material through the syringe, in a preferred embodiment, there is a gradual decrease in barrel 91 (internal) diameter at the tip of the syringe toward the bore 95. This gradual decrease better streamlines the material flow through the bore.

These syringes differ than those in the prior art in that the plunger/barrel internal diameters (and therefore, cross-sectional areas) of the prior art increase with increasing syringe size. Since the bore diameter does not change with increasing syringe size, increasing force (due to increased resistance) is required to inject the material through the bore as the syringe size/volume increases. When larger syringes (5 cc) are used to inject viscous materials that tend to thicken with time (in order to set), it is not uncommon for syringes of the prior art to break upon the forceful extrusion/injection of the material.

The kits of the present invention are tailored to adequately and precisely deliver a restorative composition into an intraosseous space such as a human vertebra when the composition has a very mobile rheology.

In general embodiments of this invention, after the operator creates a space or opening in the bone for the composition, the intraosseous space is augmented with restorative composition. The augmentation begins with an initial dam being created by a small dosage of composition via the catheter. This dam is created to prevent additional dosages of material from flowing out of the space because of a very mobile rheology. The dam is allowed to cure, the catheter is replaced, and then a second aliquot of the restorative composition is added to the dam as necessary. This aspect of the invention ensures that all openings are closed with the composition for leakage prevention. Once the second aliquot of composition has cured, additional aliquots of composition can be injected via an additional syringe containing an additional aliquot of material so that the space or opening is completely filled. It is appreciated that additional aliquots will not be necessary for all procedures. Unlike the prior art, an operator using the present invention can routinely set up a dam of material, allow it to harden, and then inject additional doses of material by replacing the catheter. The systems of the present invention uniquely accommodate for mix on demand delivery systems using a delivery gun and mix-tip.

In typical embodiments, the kits of the present invention feature tactile feedback control. When delivering a composition into a vertebra, the cannula 10 is generally inserted substantially close to, but not against, the anterior wall. Some distance is necessary between the cannula 10 and the wall so that the micro-reamer 12 can create a channel. For those embodiments featuring catheters with a side-opening 50, the composition is radially dispersed into the space even if the distal end of the catheter is in contact with the anterior wall. In other embodiments, the syringes of the present invention exemplify the tactile feedback control by allowing the user to apply constant force regardless of volume being inserted.

A number of restorative compositions can be used within the systems of the present invention. The type of composition used depends upon which procedure is being performed. In some embodiments, the system includes the injection of a plurality of materials including hydrogels, synthetic bone void fillers, polymethylmethacrylate, or replicated bone marrow. In one general embodiment, the system is a syringe filled with material. Specifically, the system is a prefabricated system of material that is directly injected into the syringe or the catheter. In another embodiment, the system for delivery comprises a sole syringe.

Once the channel is created with the micro-reamer 12, the catheter is inserted into the cannula 10 to the same depth previously occupied by the micro-reamer 12. A small amount of restorative material, between approximately 0.5–1.5 cc, is slowly injected into the catheter, via a syringe filled with restorative material, under fluoroscopic control while checking for any venous leaks. The catheter can be easily visualized under fluoroscopy either by using a radiopaque material or by adding an agent to the material that makes the material radiopaque. Should a venous leak occur, the injection is immediately stopped, and the catheter removed from the cannula 10 while the cannula remains in place. In this way the access port to the vertebra remains open. After waiting the appropriate amount of time, for example between 2 to 4 minutes, a new catheter is inserted and the injection resumed. Should another venous leak occur, the same procedure is repeated. Once there are no (more) venous leaks, the appropriate volume of material is injected. This technique allows one to make optimal use of a mix-on-demand characteristic of a restorative material, place the desired amount of material into the site, and eliminate hurrying of the procedure due to concerns of the material setting in the cannula.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A kit for delivery of a restorative composition to an intraosseous space, comprising:
   a plurality of stainless steel catheters having graded markings on an external surface thereof,
   a plurality of syringes of different volumes,
   and a plunger,
   wherein the internal diameters of each of the plurality of syringes are equal and the plunger has a diameter allowing it to move within the barrel of each interchangeably.

2. The kit of claim 1 wherein said catheter has a distal end and at least one placement orifice disposed proximate to said distal end; said placement orifice being adapted for dispensing the restorative composition radially from the catheter.

3. The kit of claim 1 further comprising a cannula with a solid handle affixed to a proximate portion of said cannula and has asymmetric halves extending outward from a bore along the axis of the cannula.

4. The kit of claim 1 further comprising a micro-reamer.

5. The kit of claim 1 further comprising a screw having a bore along the longitudinal axis of said screw.

6. The kit of claim 1 further comprising a stylet, micro-reamer, and cannula having a proximate end and distal end and a lateral surface responsive to impact blows that is fixed to the proximate end.

7. The kit of claim 1 further comprising one or more syringes having a Luer lock.

8. The kit of claim 1 wherein said cannula is divided into grades, said grades being markings.

9. The kit of claims 1 wherein said micro-reamer is divided into grades, said grades being markings.

10. The kit of claim 1 wherein the restorative composition comprises a hydrogel.

11. The kit of claim 1 wherein the restorative composition comprises a synthetic bone void filler.

12. The kit of claim 1 wherein the restorative composition comprises polymethylmethacrylate.

13. The kit of claim 1 wherein the restorative composition comprises replicated bone marrow.

14. The kit of claim 1 wherein said catheters are flexible.

* * * * *

UNITED STATES PATENT AND TRADEMARK OFFICE
CERTIFICATE OF CORRECTION

PATENT NO.    : 6,613,018 B2
DATED         : September 2, 2003
INVENTOR(S)   : Bagga et al.

It is certified that error appears in the above-identified patent and that said Letters Patent is hereby corrected as shown below:

Column 4,
Lines 42-56, delete the entire paragraph.

Column 5,
Line 9, please insert the following paragraph
-- The shaft 7 of the micro-reamer 12 is generally longer than the shaft 20 of the cannula. It can extend from about 1.0 - 3.0 cm (and all combinations and subcombinations of ranges and specific volumes therein) out of the distal tip of the cannula 10 when fully inserted. Typically, the length of the second shaft of the catheter is about equal in length to the length of the micro-reamer 12 when fully inserted into the cannula. Micro-reamers of varying lengths can be used depending on the approach an operator uses to access an intraosseous space. In certain embodiments, when accessing a vertebral space, the tip of the cannula 10 remains in the inner opening of the bone while the elongated micro-reamer 12 accesses the opposite cortex of the vertebral space. In other embodiments, the micro-reamer is shaped, bent, or made from a shape memory material, which allows extra bending, so as to create a wider channel space for the catheter. --.

Column 8,
Line 52, delete "claims" and insert therefor -- claim --.

Signed and Sealed this

Thirteenth Day of January, 2004

JON W. DUDAS
*Acting Director of the United States Patent and Trademark Office*